(12) United States Patent
Leveille

(10) Patent No.: US 6,423,249 B1
(45) Date of Patent: *Jul. 23, 2002

(54) CALIBRATION MEDIUM FOR WAVELENGTH CALIBRATION OF U.V. ABSORBANCE DETECTORS AND METHODS FOR CALIBRATION

(75) Inventor: Michael J. Leveille, Northbridge, MA (US)

(73) Assignee: Waters Investments Limited ( * ) Notice: Subject to any disclaimer, the term of this patent is extended or adjusted under 35 U.S.C. 154(b) by 0 days.

This patent is subject to a terminal disclaimer.

(21) Appl. No.: 09/599,231

(22) Filed: Jun. 22, 2000

Related U.S. Application Data

(63) Continuation of application No. 08/834,061, filed on Apr. 11, 1997.

(51) Int. Cl.[7] .............................. F21V 9/04; G02B 5/20; G01J 3/00
(52) U.S. Cl. ........................ 252/588; 252/584; 359/350; 359/361; 356/51; 356/234
(58) Field of Search ................................ 252/582, 584, 252/588, 589; 359/350, 361; 356/51, 234

(56) References Cited

PUBLICATIONS

Orignac et al., Applied Physics Lett., vol. 69, No. 7, pp. 895–897, (1996).*
Xu et al., Journal of Non–Crystalline Solids, vol. 194, pp. 235–240, (1996).*

* cited by examiner

Primary Examiner—Philip Tucker
(74) Attorney, Agent, or Firm—Brian Michaelis; John Serio

(57) ABSTRACT

The invention features an optical medium for calibrating UV absorbance detectors, methods for making such an optical medium, and methods for calibrating UV absorbance detectors using such a medium. The optical calibration medium includes a gel-sol silica glass monolith with a rare-earth dopant therein. The rare-earth dopant exhibits at least one spectral feature in at least the far UV range. The constituents of the gel-sol silica glass monolith are selected so the rare-earth doped sol-gel glass monolith exhibits a transmittance in the far UV range so each distinct spectral feature of the rare-earth dopant in the far UV range is discernable.

5 Claims, 12 Drawing Sheets

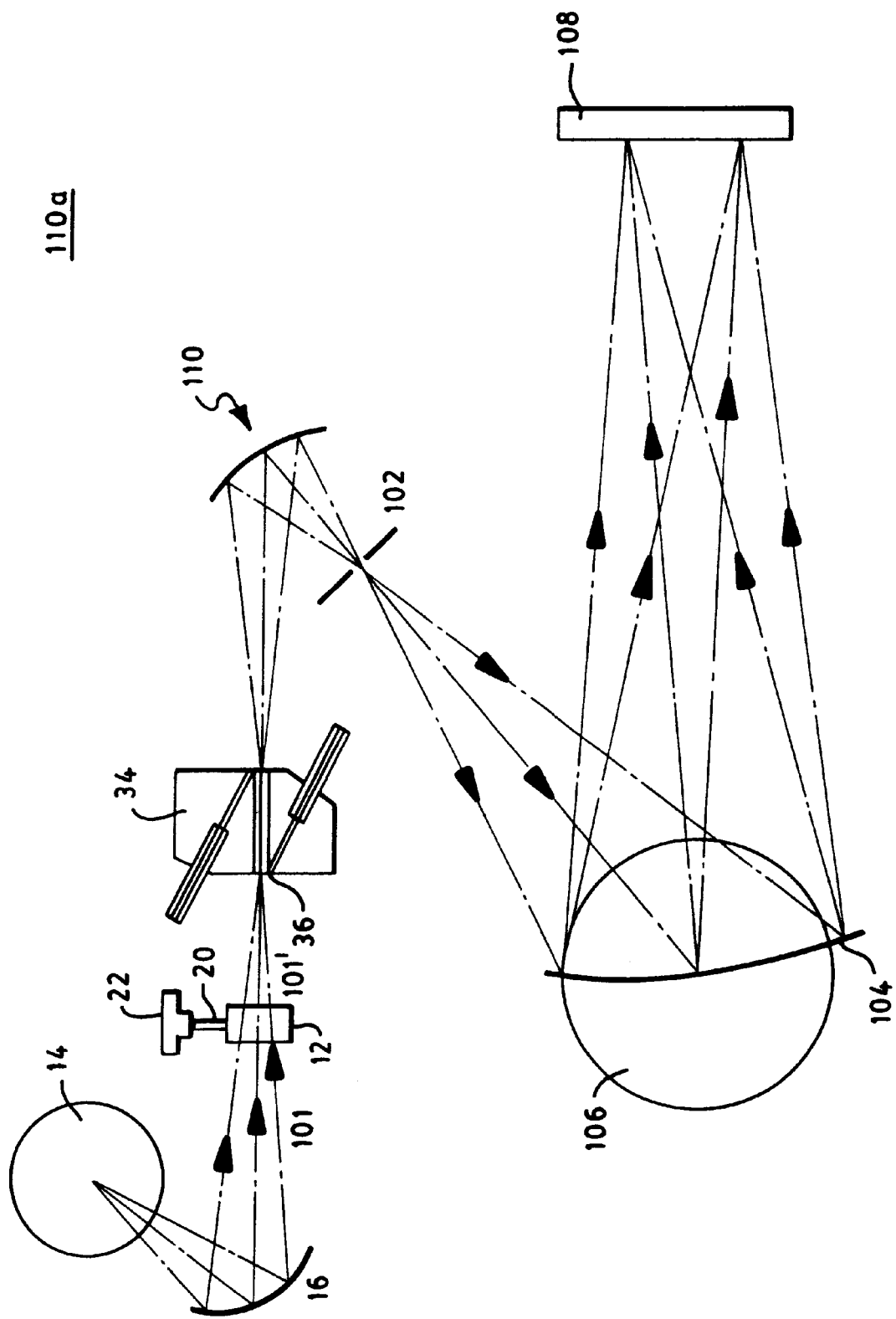

CALIBRATION MEDIUM FOR WAVELENGTH CALIBRATION OF U.V. ABSORBANCE DETECTORS AND METHODS FOR CALIBRATION

RELATED APPLICATIONS

This application is a Continuation application of U.S. Ser. No. 08/834,061 filed Apr. 11, 1997 pending, the entire teachings of which are herein incorporated by reference.

FIELD OF INVENTION

The present invention relates to techniques and mechanisms for calibration of optical analyzing devices or systems and more particularly to rare-earth doped optical mediums to calibrate UV absorbance detectors, methods for making such optical mediums and methods for calibrating devices using such optical calibration mediums.

BACKGROUND OF THE INVENTION

Ultraviolet (UV) absorbance detectors or detection systems, such as monochromator based liquid/gas chromatographic detectors or spectrographs, typically are used in manufacturing facilities, hospitals and laboratories to analyze a sample to determine its chemical composition or make-up. The sample being analyzed can be an unknown material sample, e.g., a forensic analysis sample or a sample of a known material that is analyzed to verify its chemical composition, e.g. a sample of the raw material being used in a manufacturing process (e.g., pharmaceuticals). As such, these detectors or detection systems are calibrated by the manufacturer for delivery to the user and periodically thereafter to assure the detector/detection system is repeatedly and accurately sensing the spectral emissions representative of the material sample being analyzed. There are a number of techniques that can be used for field calibration of UV absorbance detectors. For purposes of the subject application, field calibration shall be understood to mean calibration of an instrument, detector or detection system at the end users location and not in a dedicated laboratory, manufacturing or testing facility, which generally is referred to as shop or lab testing.

One calibration technique involves the use of a light source, such as mercury pen-ray lamp, having a known spectral emission to calibrate the detector or detection system (i.e., calibration light source). Such calibration light sources provide for accuracy in wavelength calibration because of the generous range of their spectral features (e.g., emission peaks). For example, the range of spectral features for a mercury pen-ray lamp covers the region from 254 nm to 580 nm. Simply, a calibration light source has a number of well defined and known spectral peaks or valleys that can be easily and repeatedly identified by a detector.

Notwithstanding its advantages, this technique is inconvenient and time consuming particularly when used for field calibration. To calibrate a UV detector or detection system in the field, it is shutdown and then disassembled so the light source normally used for analysis (i.e., analysis light source) can be removed and the calibration light source installed in its place. In other words, the detector or detection system is re-configured with the calibration light source specifically for the purposes of its calibration.

After re-configurement is completed, the detector or detection system is turned on and the calibration light source is run for a sufficient period of time to stabilize the lamp's spectral emissions. For example, it is typically recommended that a mercury pen-ray lamp be on for about 30 minutes to 1 hour before starting any calibration actions.

Thereafter, the detector or detection system is operated to determine the spectral emissions of the light source in relation to the detector's/system's performance or operation. For example, each position of a rotating diffraction grating of a monochromator detector or detection system is related to the wavelength of light reaching the UV sensor. In this way, the end user can correlate each position of the diffraction grating to a specific wavelength and the related bandpass of radiation that would irradiate a sample for analysis.

When the above actions are completed, the technician shuts the detector or detection system off, removes the calibration light source and re-installs the analysis light source. The technician then turns the detector back on and allows it to equilibrate to a stable operating condition.

The analysis light source, e.g., a deuterium lamp, typically has a characteristic spectral feature (e.g., see FIG. 5). After the unit has stabilized for purposes of spectral emissions, a quick test is typically run to see if the spectral characteristic of the analysis light source is seen where it is supposed to be. For example, the spectral emissions about and at a given rotational position of the rotating diffraction grating, corresponding to this wavelength characteristic, are evaluated to see if the position does corresponds to the wavelength of the analysis light source's characteristic.

It is not uncommon to see a technician take about 2–3 hours, and more if there are adjustments or problems, to perform the above described calibration testing process. Because of the testing process and the need for a calibration light kit, it is also not uncommon to see this type of calibration test done by the manufacturer's field representatives. As such, this technique does not allow "on-demand" tests by the end user to be performed easily or without undue complexity.

In a second technique, a holmium doped glass filter is selectively disposed between the analysis light source and a UV sensor of the system. In one configuration, a holmium doped glass optical filter is disposed between the light source and the entrance slit for the detector. In another configuration, the holmium doped glass optical filter is disposed between the detector's/system's sample cell and UV sensor. The holmium glass filter in conjunction with the analysis light source generates an emission spectrum with distinct spectral features that can be used for wavelength calibration of a spectrophotometer and some HPLC detectors. In contrast to the first calibration technique described above, the holmium glass filter based calibration technique can be incorporated into the design and function of the instrument so the user can make an "on-demand" type of test.

However, there are inherent shortcomings when using the holmium glass filter for UV instruments. Specifically, the holmium doped glass lacks far UV spectral features. Although holmium in a solution does exhibit spectral features in the range from about 240 nm to about 880 nm, as a practical matter holmium doped glass is only useful down to about 330 nm (e.g., see FIG. 6). Spectral features below 345 nm are difficult, if not impossible, to resolve because of the transmission cutoff of the base glass doped with the holmium material.

Conventional methods of doping optical glass requires the melting of the base glass, adding the required dopants and letting the glass cool and solidify. The solidified glass is then further processed (e.g., machined/ polished) to obtain the finished part geometry. To overcome the poor UV transmission characteristic inherent in the base glass material described above, one could use a base glass such as quartz or fused silica. However, the extreme high temperatures required to melt quartz or fused silica, e.g. greater than about 1800° C., restricts the selection of suitable dopants. In particular, these high temperatures essentially preclude doping base glass with a rare-earth material because the end product will not exhibit the desired spectral characteristic(s).

The absence of a useful spectral feature in the far UV range means that algorithms must be used to extrapolate the wavelength scale of the instrument over the spectral region between 190 nm and 345 nm. This is the spectral wavelength region in which the vast majority of UV absorbance detectors are operated in.

In a third technique, the detection system is initially calibrated using a calibration light source lamp at the manufacturer's site or by a field service representative in the manner described above. The end user then periodically checks calibration by using spectral features inherent in the light source used for analysis. For example, in the case of deuterium lamp, one uses the 486 nm and 656 nm spectral lines (see FIG. 5). Although this method is convenient and accurate for the spectral region close to and between these lines, its accuracy and repeatability outside of these areas, particularly when dealing with wavelengths below about 350 nm, is suspect. This method or technique also relies on algorithms that extrapolate over a much larger spectral region than when using the holmium filter technique described above.

In another technique, a chemical standard is periodically analyzed by the detection system. For example, an erbium perchlorate liquid sample is analyzed and a spectral emission or characteristic as a function of the operation of the detection system is obtained. The end user uses the obtained spectral characteristic of the controlled sample to calibrate the instrument, detector or detection system. This test is similar to the validation tests done periodically to independently establish the spectral performance and/or the operability of the detection system.

In a validation test, the spectral emissions as determined by a calibrated detector/system is compared with the known spectral emission characteristic for the sample. If the comparison matches within a given degree of accuracy, then the detector's or detection system's results are considered to be validated and reliably accurate. However, if the comparison does not match within the required degree of accuracy, then the detector/system must be re-calibrated, repaired or replaced. Additionally, any test or analysis previously performed by the detector or detection system may be suspect.

Although chemical standards tests are accurate and can be used to calibrate as well as to validate a detector's performance, they are time consuming and expensive, particularly if performed on an "on-demand" basis, e.g., day to day calibration checks.

There also is described in U.S. Pat. Nos. 4,099,883, 4,106,857 bandpass filters that include rare-earth material constituents.

For these bandpass filters the spectral characteristics of combinations of various rare-earth materials are used to establish or define the cut-off or boundary for a given bandpass of non-UV wavelengths. There also is described in U.S. Pat. Nos. 5,311,525, 5,452,124, 5,467,218, 4,481,399, 5,502,592, 5,491,581, 5,067,789, 5,524,118, 5,474,588 and 5,526,459 a number of applications where a fiber, used for laser light communications, is doped with a rare-earth material.

SUMMARY OF THE INVENTION

The present invention features an optical medium uniquely adapted and configured for insitu calibration of UV absorbance detectors by end users or manufacturers service representatives. The invention also features methods for making such an optical medium as well as methods for calibrating UV absorbance detectors using the optical calibration medium of the invention. Additionally, the invention features a UV absorbance detector or system uniquely configured to facilitate performance of such a calibration by the user without disassembly.

The optical medium for calibration of UV absorbance type detectors, according to the present invention, includes a gel-silica base glass monolith and a rare-earth material dopant therein. In a particular embodiment, the gel-silica base glass monolith includes a type IV porous gel-silica base glass and more particularly includes a type V dense gel-silica base glass. The type IV doped gel-silica base glass has a UV transmittance of about 50% at 250 nm as compared to about a transmittance of about 3–4% for the base glass used for prior art holmium doped glass filters. Further, the characteristics of the rare-earth dopant in the far UV remain generally discernable.

In a particular embodiment, the dopant is selected from the group consisting of atoms of the rare-earth group that have partially filled 4f electron shells (namely from cerium, atomic number 58, to ytterbium, atomic number 70). More particularly, the rare-earth materials selected for use as dopants are those exhibiting a wide range of spectral features, preferably over a range from about 190 nm to about 700 nm and more particularly, from about 220 nm to about 700 nm. Preferably, the rare-earth dopants have at least one distinct spectral feature in the far UV, more particularly, in a range from about 190 nm to about 300 nm. More preferably, the rare-earth dopant is erbium, atomic number 68, having spectral features in a range from about 190 nm to about 650 nm and a distinguishable spectral feature at about 257 nm.

The above described optical medium for calibration of UV absorbance type detectors is made by a process including steps of mixing a slurry (sol) including silica, casting the sol into a rough final desired shape, allowing or causing the sol to solidify to produce a gel, aging the gel, drying the gel to remove the liquid phase and densifying the dried gel. The process further includes the step of doping at least one of the slurry or the gel with a rare-earth dopant. More particularly, doping the slurry or gel with erbium, in an exemplary embodiment, erbium nitrate. In a particular embodiment, the step of mixing includes adding the rare-earth dopant to the slurry being mixed. In another embodiment, the process further includes the step of impregnating the dried gel with the rare-earth dopant.

Preferably, the steps of aging, drying and densifying are performed under conditions that yield at least a type IV (porous) gel-silica base glass monolith having good far UV transmission characteristics. More particularly, the highest temperature used during these steps of aging, drying and densifying is about 900° C. or less.

In a more particular embodiment, the optical medium of the invention is made by a process including steps of hydrolyzing and polycondensing one or more oxide precursors to form a sol including a plurality of oxide particles suspended in a liquid; casting the sol into a mold, gelling the sol by cross-linking oxide particles to form a gel; aging the gel to form an aged gel; subjecting the aged gel to a drying treatment to remove liquid from pores of the aged gel to form a dried gel; and densifying the dried gel to form an oxide sol-gel monolith. The drying treatment includes steps of (i) heating the aged gel in a mid to high humidity environment and then (ii) heating the aged gel in a low humidity environment. The foregoing steps also being set forth in U.S. Pat. No. 5,076,980, the teachings of which are incorporated herein by reference.

The above described process further includes the step of doping at least one of the sol or the gel with a rare-earth dopant. More particularly, doping the sol or gel with erbium, in an exemplary embodiment, erbium nitrate. In a particular embodiment, the step of hydrolyzing and polycondensing includes adding the rare-earth dopant, e.g., erbium to form the sol. In another embodiment the process further includes the step of impregnating the dried gel with the rare-earth dopant.

Preferably, the steps of aging, subjecting the aged gel to a drying treatment and densifying are performed under conditions that yield at least a type IV (porous) gel-silica base glass monolith. More particularly, the highest temperature used during these steps of aging, drying and densifying is less than about 900° C.

As indicated above, the invention also features a method for calibrating any one of a number of UV absorbance detectors having a light source with spectral emissions over a range of wavelengths and a sensor being responsive to at least a portion of the spectral emissions from the light source. The calibration method of the instant invention includes steps of providing a rare-earth doped gel-silica base glass monolith, selectively disposing the rare-earth doped gel-silica base glass monolith between the light source and the sensor, sensing the radiation passing through the rare-earth doped gel-silica base glass monolith, identifying spectral features unique to the light source and the rare-earth doped monolith and establishing a relationship between operation of the UV absorbance detector and a wavelength to be sensed using the identified spectral features.

In one specific embodiment, the rare-earth doped gel-silica base glass monolith is selectively disposed between the light source and an entrance slit of the UV absorbance detector. For this embodiment, the detector senses transmission. In another specific embodiment, the rare-earth doped gel-silica base glass monolith is selectively disposed between the sensor and the sample cell of the UV absorbance detector. For this embodiment, the detector senses absorbance.

For monochromator type UV absorbance detectors, the detector further includes a mechanism that selectively isolates a specific wavelength bandpass from the range of wavelengths being emitted by the light source. Additionally, the above described calibration process further includes the step of actuating the mechanism in stepwise fashion to sequentially isolate a bandpass over the range of wavelengths.

For spectrographic type UV absorbance detectors, the detector further includes a diffraction grating between the light source and the sensor, the sensor is arranged to receive the spread spectrum radiation from the diffraction grating and the sensor is configured to separately detect radiation in a plurality of bandpasses. Further, the step of selectively disposing the rare-earth doped gel-silica base glass monolith includes selectively disposing the monolith between the light source and an entrance slit of the UV absorbance detector so radiation passing through the monolith impinges on the diffraction grating. Additionally, the step of sensing includes simultaneously and separately sensing in a plurality of bandpasses the spread spectrum radiation from the diffraction grating.

In a particular embodiment, the rare-earth doped gel-silica base glass monolith being provided is an erbium doped gel-silica base glass monolith. Further, the step of sensing includes sensing spectral emissions in the far UV and the step of establishing relationship between operation and wavelength includes establishing a relationship with the wavelengths in the far UV based on the spectral emissions being sensed in the far UV.

As noted above, also featured is a UV absorbance detector or detection system incorporating a rare-earth doped gel-silica base glass monolith of the instant invention. The features of such a detector or system are hereinabove described, and as such, will not be repeated again here. In a preferred embodiment, such a detector or system further includes a mechanism for selectively interposing the rare-earth doped gel-silica base glass monolith between the system's light source and the sensor. In this way, an end user can easily perform a calibration activity without having to turn the detector or system off as is done with the prior art calibration lamp technique. Such a mechanism is remotely operated either manually or by a remote actuator, for example a rotatory air-operated or electrically operated actuator.

Features of the instant invention include an optical medium that, in conjunction with the analysis light source of a UV absorbance detectors, generates a useful emission spectrum. This emission spectrum is useable to perform "on-demand" calibrations of such UV absorbance detectors. In particular, the emission spectrum being generated covers a wide range of wavelengths, for example over the range from about 190 nm to about 700 nm. More particularly the spectrum being generated includes spectral features in the far UV range or in the range from about 190 nm to about 300 nm. Other features of the invention include a method of making a rare-earth doped optical medium that exhibits the above described characteristics and a method for calibrating such UV absorbance detectors using the a rare-earth doped optical medium of the invention.

BRIEF DESCRIPTION OF THE DRAWINGS

FIG. 3A is an optical schematic diagram of an exemplary spectrograph including the calibration medium of the invention;

DESCRIPTION OF THE PREFERRED EMBODIMENT

Figure 1A:
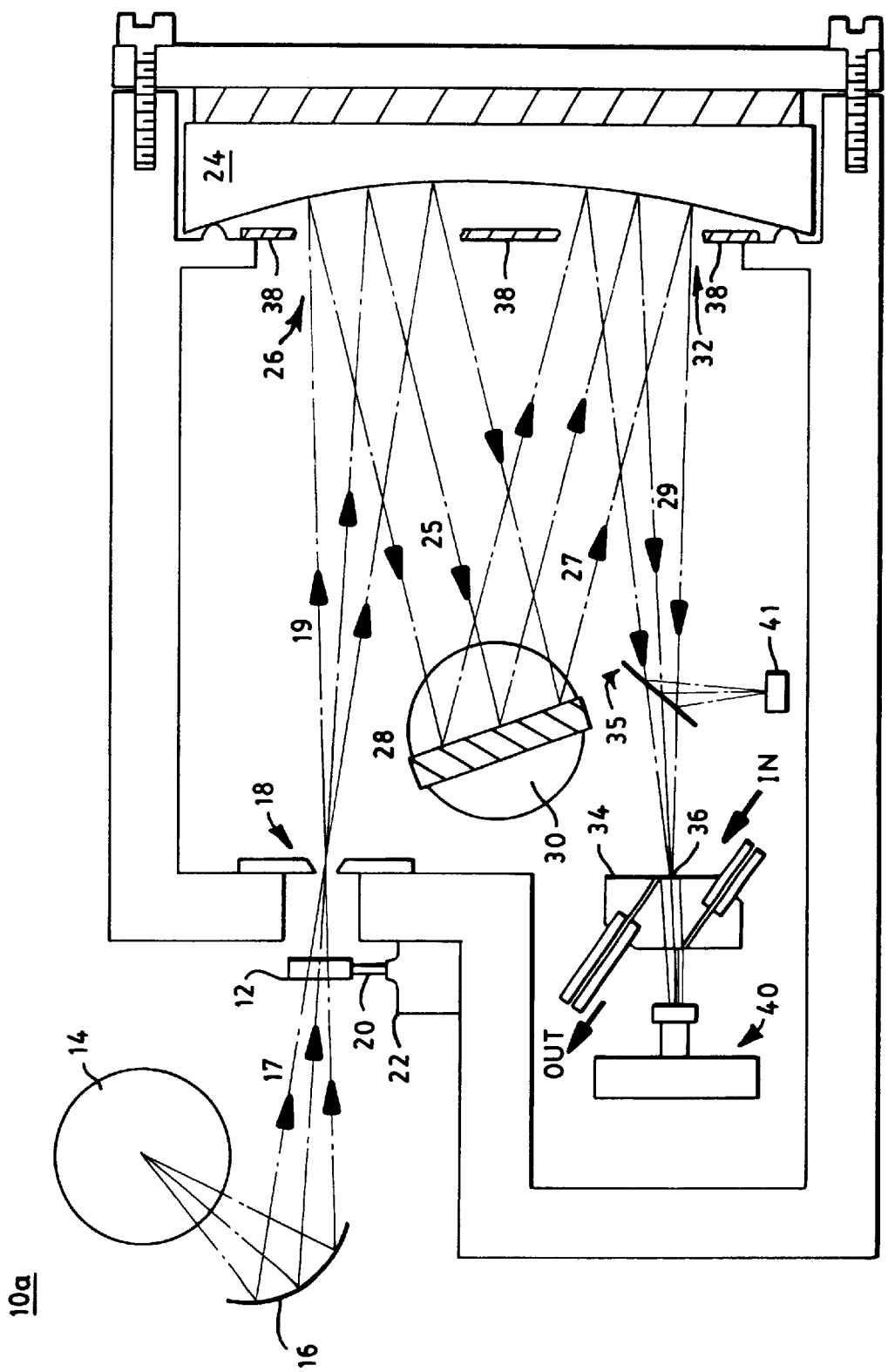
FIG. 1A is an optical schematic diagram of an exemplary monochromator absorbance detector including the calibration medium of the invention.
Figure 2A:
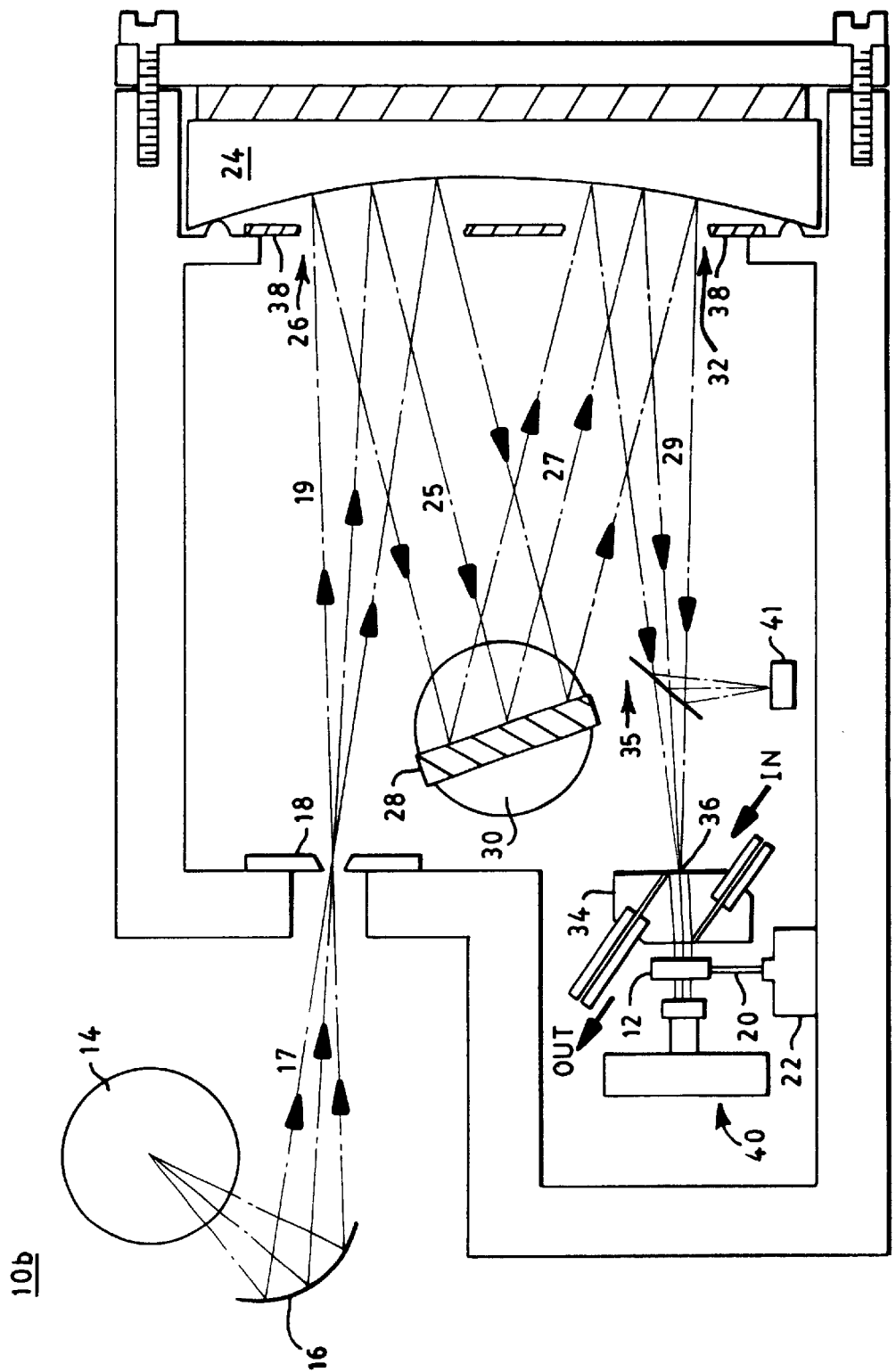
FIG. 2A is an optical schematic diagram of an alternate configuration for the detector of FIG. 1A.

Referring now to the various figures of the drawing wherein like reference characters refer to like parts, there is shown in FIGS. 1A, B and FIGS. 2A and B monochromator type UV absorbance detectors 10a, 10b including a calibration medium 12. Also, there is shown in FIGS. 3A–D spectrograph type detectors 100a, 100b that include a calibration medium 12. Preferably, the calibration medium 12 according to the instant invention is a rare-earth doped gel-silica base glass monolith that includes a gel-silica base glass monolith and a rare-earth material dopant therein. A gel-silica base glass monolith and a rare-earth doped gel-silica base glass monolith generally describe optical mediums that are formed using a sol-gel process instead of the more conventional glass forming/doping process of melting the base glass, adding the required dopants and letting the glass cool and solidify. As provided hereinafter, using a sol-gel process to make the calibration medium 12 advantageously yields an optical base glass, that has good UV transmission characteristics and can be doped with rare-earth materials.

In particular embodiment, the gel-silica base glass monolith is a type IV (porous) gel-silica base glass, which exhibits a UV transmission about 10 times higher at 250 nm than the base glass used for holmium doped glass filters. More particularly the transmittance of the type IV (porous) gel-silica base glass is greater than or equal to 50%. This improved transmission as compared to prior art holmium doped glass filters, allows the rare-earth optical features or characteristics in the far UV to remain generally discernable (i.e., good contrast) and usable for calibration purposes. This type of base glass, although having good optical properties, is typically not sufficiently dense to be considered a fluid pressure boundary. In another embodiment, the gel-silica base glass monolith is a type V dense gel-silica base glass, which has far UV transmission characteristics like that of quartz and which exhibits fluid pressure boundary capabilities.

The minimum transmittance of a gel-silica base glass monolith for use as a calibration medium 12 is dependent upon a number of factors including system bandwidth and system sensitivity (e.g. sensitivity of the detector assembly). For purposes of the instant invention, the gel-silica base glass monolith should transmit sufficient far UV radiation so as to maintain a good contrast between the at least one spectral feature in the far UV, for the rare-earth dopant, and background light. For example, is the gel-silica base glass monolith for a monochromator or spectrograph type UV absorbance detector application having a 3–5 nm system bandpass, should exhibit a transmittance of 25% or greater.

The dopant is a material that includes or consists of atoms of the rare-earth group that has partially filled 4f electron shells (namely from cerium, atomic number 58, to ytterbium, atomic number 70). For the calibration medium 12, the rare-earth materials selected for use as dopants are those that exhibit a wide range of spectral features, over the range from about 190 nm to about 700 nm, more specifically in the range from about 200 nm to about 700 nm and more particularly in the range from about 256 nm to about 656 nm. More preferably, the rare-earth dopants also have at least one distinct spectral feature in the far UV, more particularly, in the range of from about 190 nm to about 300 nm.

Figure 4:
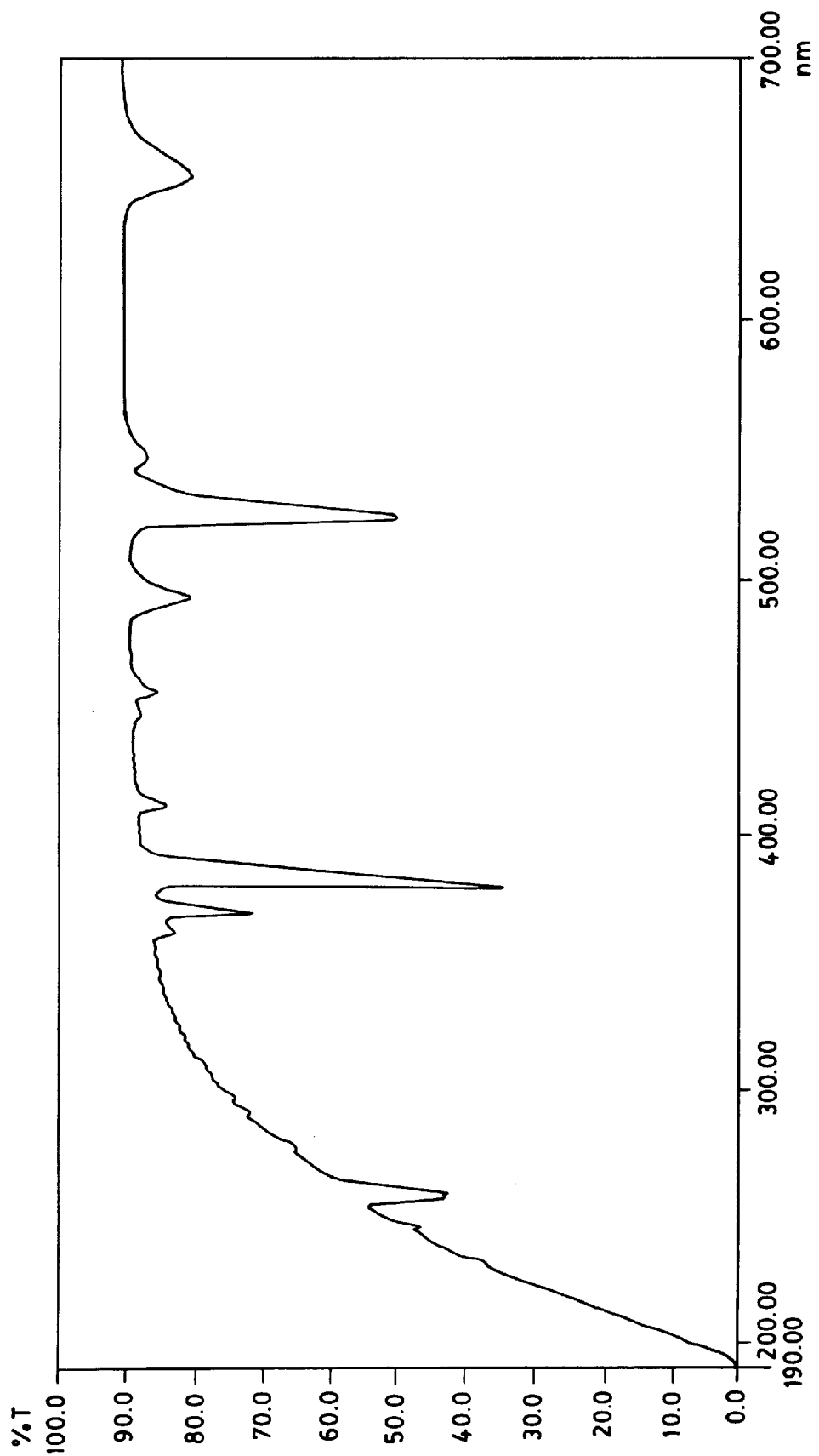
FIG. 4 is an exemplary emission spectrum for erbium doped silica.

In a specific embodiment, the rare-earth dopant is erbium, atomic number 68, having spectral features in the range of from about 250 to about 650 nm and distinguishable spectral features at about 257 nm, 379 nm and 521 nm. In a particular embodiment, the dopant is erbium nitrate. Preferably, the doped optical medium exhibits the optical features or characteristics as shown in FIG. 4. The dopant concentration is adjusted to provide the needed contrast between the far UV spectral feature(s) and the background light so the composite light spectrum is useable for purposes of calibration. In particular embodiments, the quantity of erbium in the calibration medium 12 is in the range of from about 6% to about 10%.

An erbium doped gel-silica base glass monolith is particularly advantageous as the calibration medium 12, because it provides several approximately equally spaced calibration points (i.e., spectral features) throughout the wavelength range from about 190 nm to about 700 nm, more particularly from about 220 nm to about 700 nm. As such, a detector or system calibrated using such a calibration medium would be as accurate as one which had been calibrated using the calibrated light source technique. Moreover, the erbium dope monolith includes a calibration point deep in the UV, at about 257 nm, which is in the spectral region were a large number of end users operate UV absorbance detectors. This further improves the accuracy of the detector or system, particularly for measurements in the far UV.

As indicated above, the rare-earth doped gel-silica base glass monolith comprising the calibration medium, is made using a sol-gel process. The sol-gel process generally includes the steps of mixing a slurry (sol) including silica, casting the sol into the rough final desired shape, allowing or causing the sol to solidify so as to produce a gel, aging the gel, drying the gel to remove the liquid phase and densifying the dried gel. In the present invention a rare earth dopant is added to the slurry, when it is being mixed, or to the gel. More specifically the dried gel, is impregnated with the rare-earth dopant. In a specific embodiment the dopant is erbium such as a erbium nitrate solution.

As noted above the steps of aging, drying and densifying are performed under conditions that yield either a type IV (porous) gel-silica base glass monolith or a type V (dense) gel-silica base glass monolith. In an exemplary embodiment, the highest temperature used during these steps of aging, drying and densifying to yield a type IV (porous) rare earth doped gel-silica base glass monolith is about 900° C. or less.

In a more particular embodiment, the optical medium of the instant invention is made using a sol-gel process described in U.S. Pat. No. 5,076,980, the teachings of which are incorporated herein by reference. This process includes the steps of hydrolyzing and polycondensing one or more oxide precursors, such as silicon oxide and silicon alkoxide, to form a sol including a plurality of oxide particles suspended in a liquid. To yield a calibration medium 12 of the invention, materials are selected so the monolith being produced exhibits the desired far UV transmission characteristics. In one embodiment, the step of hydrolyzing and polycondensing also includes adding a rare-earth dopant to form a rare-earth doped sol. As above, in a specific embodiment, the rare-earth dopant is erbium.

The sol is then cast into a mold and the sol in the mold is gelled by cross-linking the oxide particles to form a gel. In this way, the resultant gel takes the shape, configuration and surface finish of the mold. Typically the gelling step is carried out at a temperature between about the freezing point and the boiling point of the sol for a specified time period based upon the temperature.

The gel is then preferably transferred to an aging oven to form an aged gel. During the aging process, liquid is expelled from the gel and the strength of the gel is typically increased many times. Also, during the aging process the solidified gel shrinks. The aging step is typically carried out at a temperature between about the freezing point of the interstitial liquid of the gel and up to about 250° C. The time required for such aging depends upon the temperature used and the size of the monolith being produced.

The aged gel is then subjected to a drying treatment to remove liquid from the pores of the aged gel to form a dried gel. This step can proceed directly from the aging step or the aged gel may be cooled to room temperature before continuing onto the drying step. This drying treatment includes the steps of (i) heating the aged gel in a mid to high humidity environment and then (ii) heating the aged gel in a low humidity environment.

Typically, the aged gels are placed in a oven in which the temperature and the atmospheric conditions, specifically the humidity, is directly or indirectly controlled, preferably directly controlled by a microprocessor. Generally, the drying treatment is carried out a temperature of from about room temperature to about 200° C. During step (i) the humidity is typically maintained at between about 50% and 100% and during step (ii) the temperature in the oven is typically raised to about 200° C., preferably to about 160° C. and the humidity is decreased to between about 50% relative humidity and less than about 5 parts per million. If the sol is not formed with a rare-earth dopant therein, then following the step of drying the dried gel is impregnated with a rare-earth dopant, e.,g., erbium.

The rare-earth doped dried gel is then densified to form a rare-earth doped oxide sol-gel monolith having the desired optical and structural properties. That is, densification is carried out for the period of time and under temperatures to produce either partially densified, e.g., porous, or fully densified sol-gel monoliths. For a type IV (porous) sol-gel monolith, the rare earth dried doped gel is partially densified. Typically, densification is carried out by heating the dried gels in a furnace or oven to a temperature between about the maximum of the drying temperature and about 1400° C. Preferably, the maximum temperature used for densification is less than about 900° C. In one embodiment, densification is carried out in a flow of dried atmospheric air, inert gas or a dried gas mixture of oxygen, chlorine or fluorine.

The above described sol-gel processes yield a rare-earth doped gel-silica base glass monolith that has the desired far UV optical characteristics. The monolith produced also exhibits the spectral features or characteristics required so it can be used as a calibration medium 12 in the below described calibration methods and detection systems/detectors. More particularly, when the monolith is doped with erbium, the doped monolith exhibits spectral features in the range of from about 250 nm to about 650 nm and exhibits a spectral feature at about 257nm.

Figure 1B:
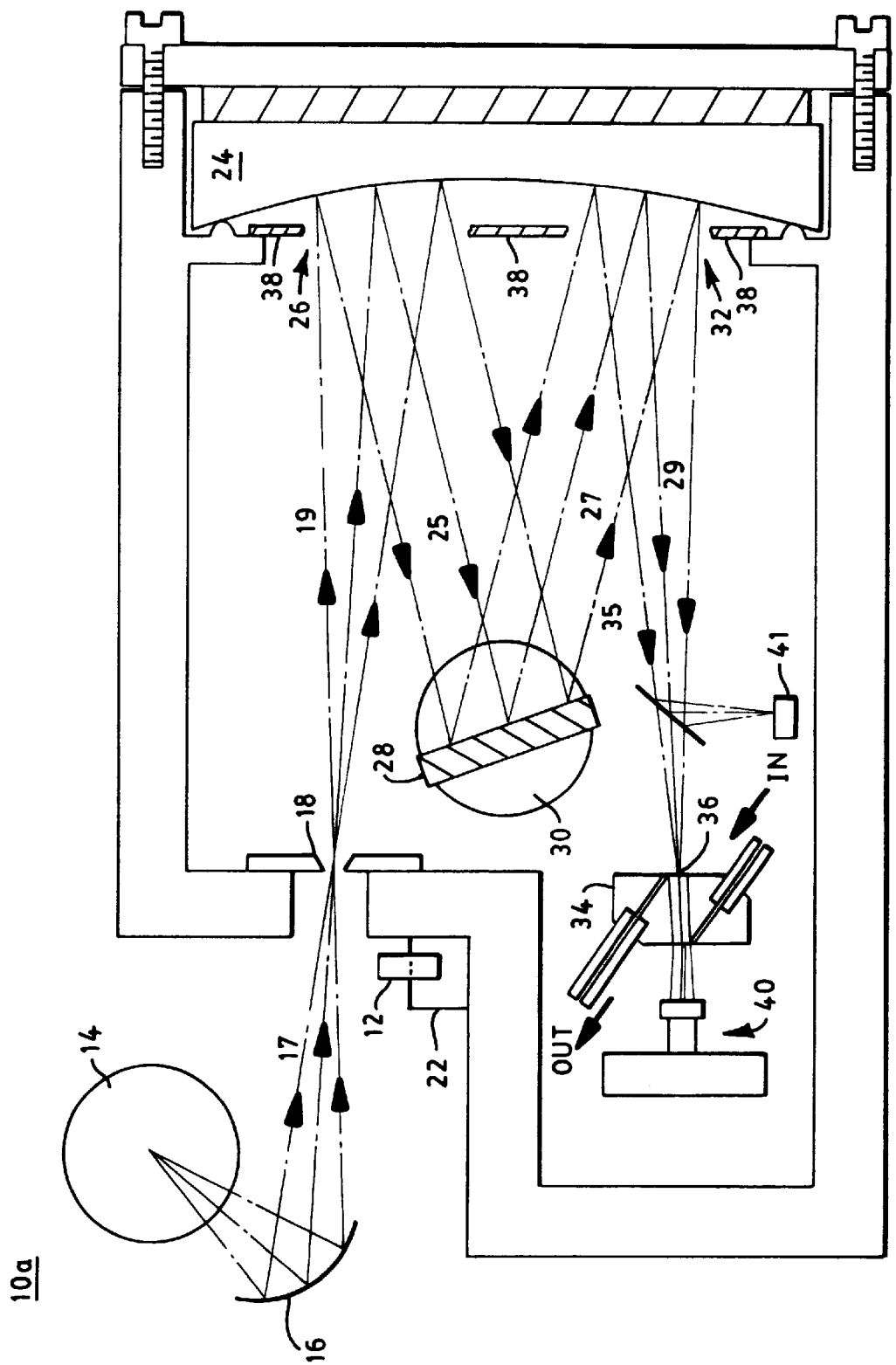
FIG. 1B is an optical schematic diagram of the detector of FIG. 1A when configured for analysis.

Now referring specifically to, FIGS. 1A and B there is shown an exemplary calibratable monochromator type UV absorbance detector 10a that includes the calibration medium 12. The calibration medium 12 is mounted to an arm 20 that is interconnected to an actuator 22 so the calibration medium is selectively disposable in either of two positions. When in the first position, as shown in FIG. 1B, the calibration medium 12 is out of the light beam 17 and the detector 10a is configured for analysis of material samples. In this position, the light (UV, visible and/or IR) from the light source 14 is focused by a focusing mirror 16 onto an entrance slit 18. When in the second position, as shown in FIG. 1A, the calibration medium 12 is in the light beam 17 and the detector 10a is configured for calibration. In this position, the calibration medium 12 is disposed between the light source 14 and the entrance slit 18 and the light from the focusing mirror 16 is focused through the medium and onto the entrance slit.

Referring now to only FIG. 1B, the light rays 19 exiting the entrance slit 18 strikes a large spherical mirror 24 that is at a predetermined and fixed distance from the entrance slit 18. The light rays 19 strikes the mirror 24 at a first position or location 26 and a collimated light beam 25 is reflected therefrom towards a plane diffraction grating 28. The diffraction grating 28 is mounted upon a rotatable mount 30, where the axis of rotation is at a fixed position and distance from the mirror 24. In an exemplary embodiment, the mirror is located about one (1) focal length from the entrance slit 18 and the axis of rotation is located centrally with respect to the curvature of the mirror at a distance of about ¾of the focal length.

The collimated light beam 25 hits the grating 28 so that a collimated beam of diffracted light 27 with a selected wavelength is directed from the grating towards a second location 32 of the mirror 24. The selected wavelength (i.e., the center wavelength of a bandpass of diffracted light) is dependent upon a number of factors including the groove density of the grating 28, the angle of the grating and manufacturing tolerances. Typically, the rotatable mount 30 is controlled so it is rotated in step wise fashion in equal angular increments. As discussed below, a calibration process is performed to establish a relationship between each angular position of the rotatable mount 30 (e.g., the number of steps of rotation) and the wavelength of the diffracted light 29 at each step or angular position. As is known in the art, a specific wavelength can be selected for analysis by rotating the mount 30 to a specific angular position or step.

The light beam 29 leaves the second location 32 and is directed towards a beam splitter plate 35. A small percentage of the light beam 29 is directed by the splitter plate 35 towards a reference photodetector 41. The remaining light is directed towards the flowcell 34. More specifically, the light beam 29 is brought to focus at an entrance lens 36 of the flow cell 34. The flow cell entrance also constitutes an exit slit of the monochromator. The rays of light which enter the flow cell 34 pass through the fluid (i.e., liquid or gas) sample to be analyzed. As provided below, when the detector is being calibrated, a neutral sample is located in the flow cell 34.

The arrangement of the entrance slit 18, the mirror 24, the diffraction grating 28 and the flow cell entrance or monochromator exit slit provide a mechanism for establishing the bandwidth of the light that can impinge upon the material sample located within the sample cell 34. In an exemplary embodiment, the detector 10a also includes a mask 38, proximate the arcuate surface of the mirror 24, to control stray light. In a specific embodiment, the mask 38 covers the arcuate or spherical surface of the mirror 24 except for the areas comprising the first and second locations 26, 32 whereat light is reflected back by the mirror 24.

The light passing through the sample being analyzed exits is the flow cell through an exit window and impinges upon a photodetector assembly 40. Typically, such an assembly 40 includes a photodetector, that provides an output signal representative of the light impinging thereupon, and an amplifier that amplifies the signal output for subsequent processing, such as digitization, measurement and display, as is known in the art. When the detector 10a is configured for analysis, this information is used by the end user to identify the chemical constituents or composition of the sample being analyzed as is known in the art.

As indicated above, the detector 10a is calibrated so a relationship is established between the various angular positions of the rotatable mount 30 and the wavelength of the light being diffracted by the grating 28 and impinging on the flow cell entrance window 36. In the present invention, and with reference to FIG. 1A, calibration of the detector 10a is begun by moving the calibration medium 12 into the light beam 17 from the light source 14 and preferably placing a neutral sample in the flow cell 34.

Figure 5:
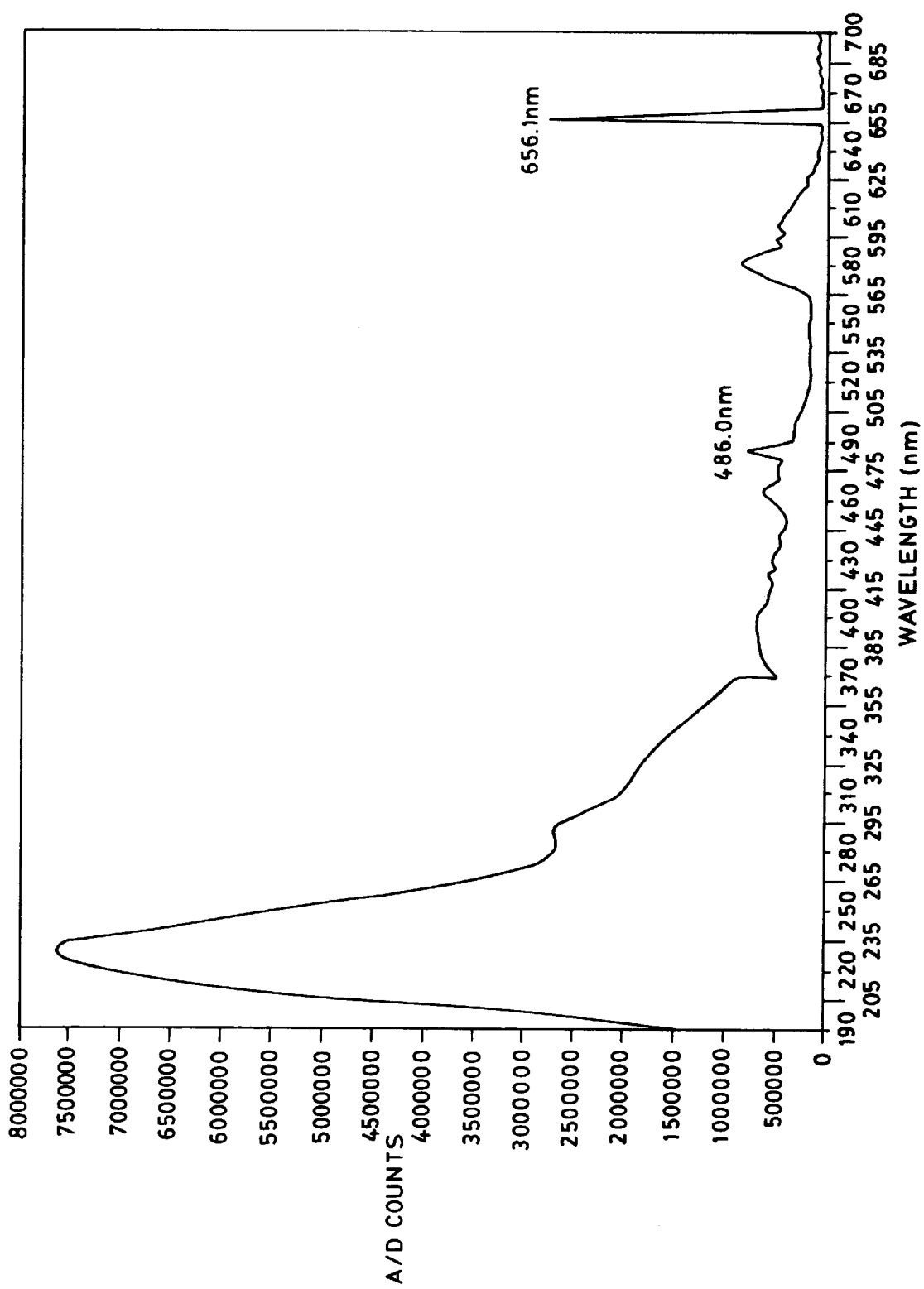
FIG. 5 is an exemplary emission spectrum for a deuterium light source.
Figure 6:
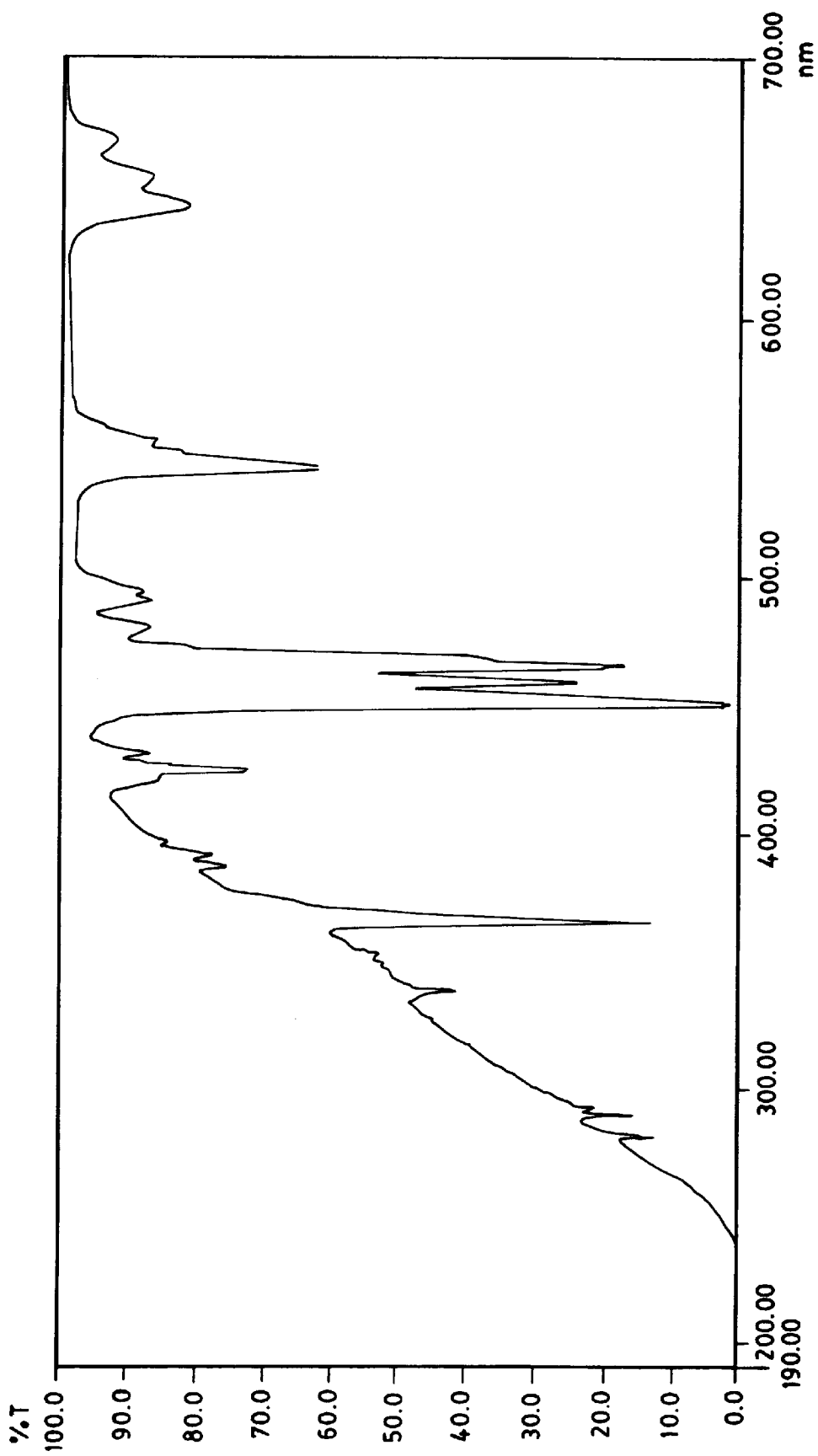
FIG. 6 is an exemplary emission spectrum for a holmium doped glass.
Figure 7:
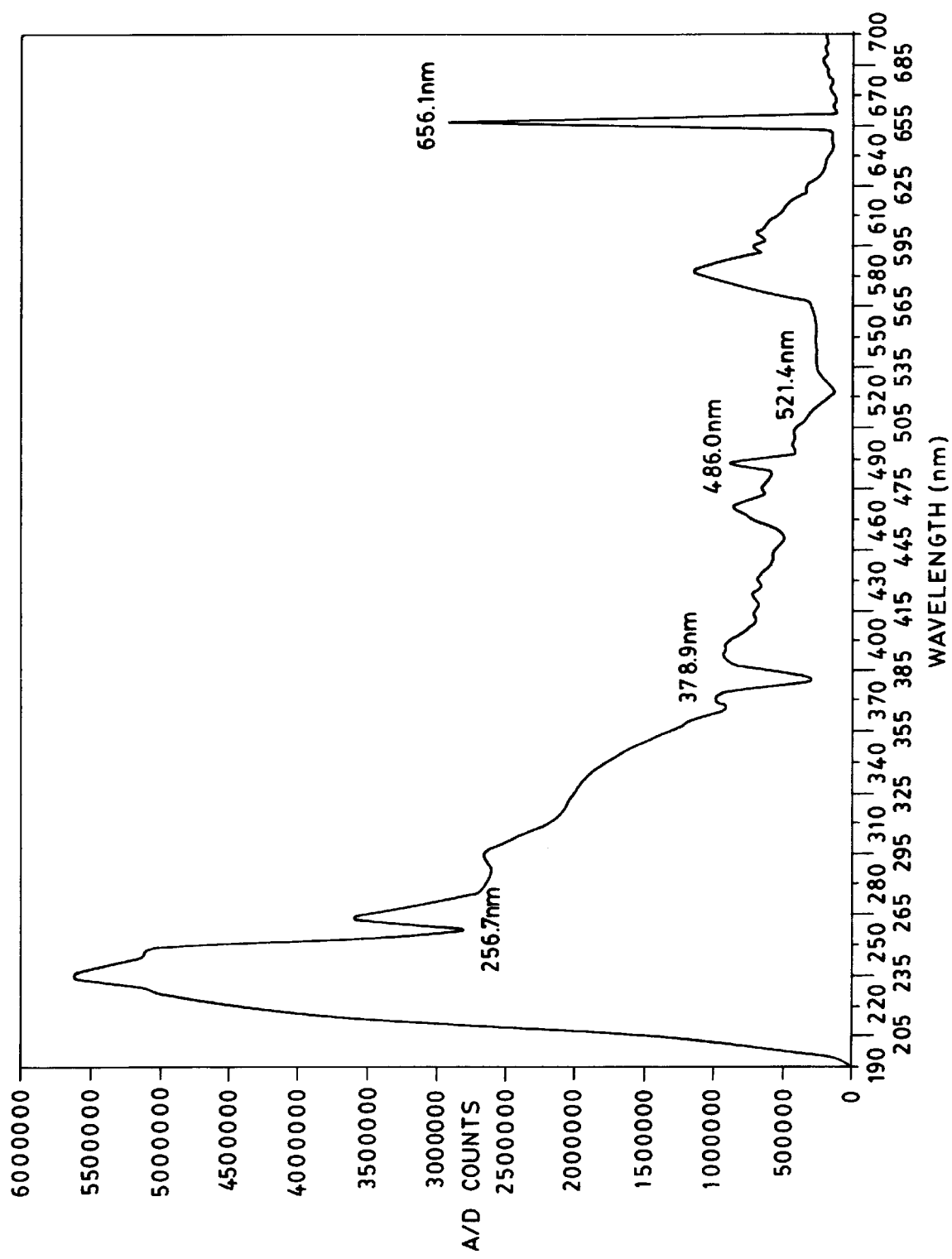
FIG. 7 is an exemplary emission spectrum combining the deuterium light source and the erbium doped silica.

The calibration medium 12 of the invention is a rare-earth doped gel-silica base glass monolith that exhibits a known absorbance spectrum. This known absorbance spectrum includes a plurality of spectral features that extend in the range of wavelengths of between from about 190 nm to about 700 nm, more specifically in the range from about 200 nm to about 700 nm, and more particularly in the range from about 256 nm to about 656 nm. Thus, the light exiting the calibration medium 12 will have a composite light spectrum that includes a plurality of spectral features such as that shown in FIG. 7. This composite light spectrum is essentially a combination of the known absorption spectrum of the medium (see FIG. 4) and the emission spectrum of the light source (see FIG. 5). As provided in the discussion above regarding FIG. 1B, the light having this composite light spectrum impinges upon the diffraction grating 28.

The end user, field service representative or technician rotates the rotatable mount 30 in step wise fashion to a specific position so one of the wavelengths of the composite spectrum is selected. As provided above, the light beam 29 of the selected wavelength light is then directed so it is detected by the photodetector assembly 40. The technician then rotates the rotatable mount 30 step wise to the next position and repeats the above. This process is repeated until at least the desired wavelengths for analysis have been covered. The technician, using this data then establishes the relationship between motion of the rotatable mount and the wavelengths which can be diffracted by the diffraction grating 28 to the second location 32 of the mirror.

After completing the above calibration process of the detector 10a, the technician actuates the actuator 22 to return the calibration medium 12 to the first position so it does not affect the light beam 17 nor affect the spectral emissions of the light source 14. As can be seen from the foregoing, the capability of selectively moving the calibration medium 12 in and out of the light beam 17 from the light source provides a means by which the end user can easily perform an "on-demand" calibration of the detector. Moreover, such a calibration can be performed and the detector quickly reconfigured to perform sample analysis without the down time required when using the prior art calibrated spectral light source technique.

The actuator 22 is any one of a number of actuators known in the art, including mechanical, electrical and air-operated rotary actuators, that move an object along an arcuate path. The actuator 22 provides a mechanism by which the detector 10a can be easily calibrated by the end user or a field service representative and without requiring the need for specialized equipment (e.g., a spectral calibrated light source). Although a rotary type of actuator is illustrated this is not a limitation, as the mechanism for moving the calibration medium can be any of a number of devices known in the art that selectively moves an object back and forth between two positions (e.g., a sliding type of devices).

Referring now to FIGS. 2A,B there is shown an optical schematic diagram of an alternate configuration for an exemplary calibratable monochromator type absorbance detector 10b. In this configuration or arrangement, the calibration medium 12 is located so that in the second position, as shown in FIG. 2A, it is disposed between the sample cell 34 and the photodetector assembly 40. Also, in this configuration the spectrum of the light that impinges upon the sample cell 34 is that of the light source 14 only. In all other respects the above discussion regarding the structure, operation and calibration of the detector 10a of FIGS. 1A,B applies equally to the detector 10b illustrated in FIGS. 2A,B.

Although the foregoing has been described in terms of a manual operation by a technician, this is not a limitation. It is within the scope of the instant invention for a detector 10a,10b of either embodiment to be configured with a digitizer, a central processing unit, storage memory and an applications program(s) that automatically rotates the calibration medium into and out of the light beam, rotates the rotatable mount 30 in a step-wise fashion, acquires and analyzes the spectral data and generates a look up table with the relationship between wavelength and the position of the rotatable mount 30.

Figure 2B:
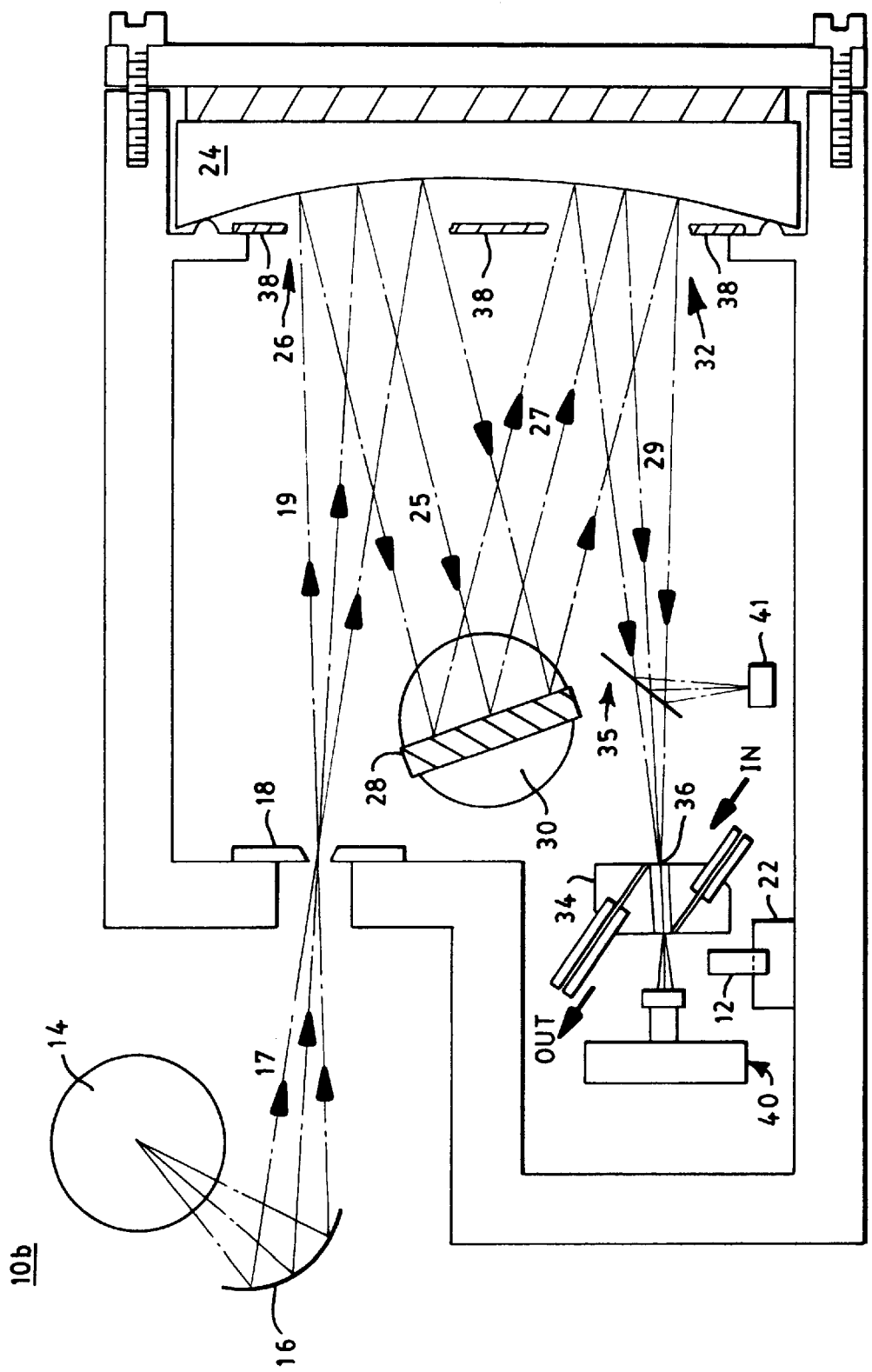
FIG. 2B is an optical schematic diagram of the detector of FIG. 2A when configured for analysis.
Figure 3B:
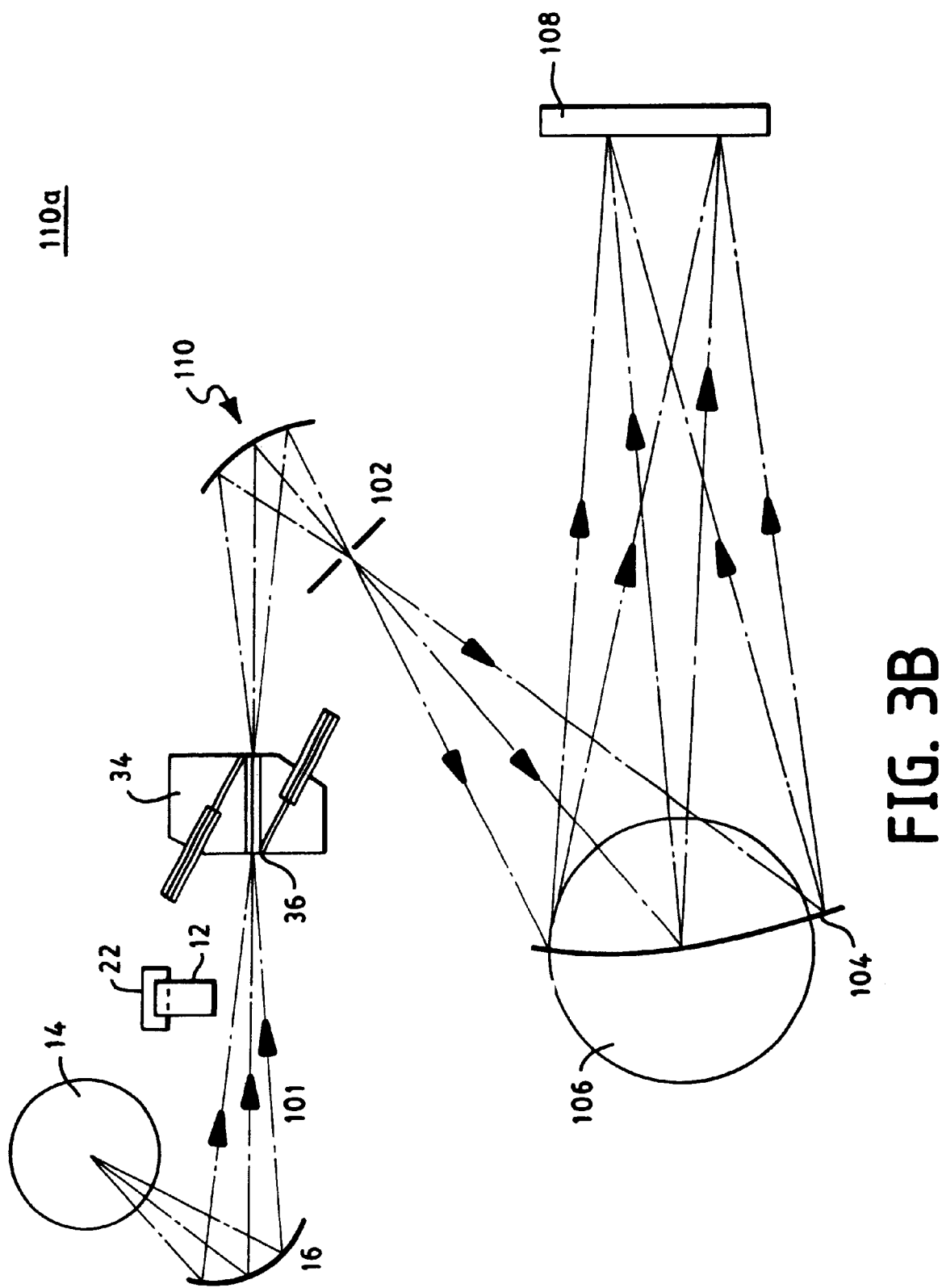
FIG. 3B is an optical schematic diagram of the spectrograph of FIG. 3A when configured for analysis.

There is shown in FIGS. 3A and B an exemplary spectrograph type detector 100a including a selectively positioned calibration medium 12 that is mounted to an arm 20 interconnected to an actuator 22. As is provided in the foregoing, the actuator 22 selectively moves the calibration medium 12 back and forth between a first and second position as shown respectively in FIGS. 3A and B. The configuration of the detector 100a when it is being calibrated is illustrated in FIG. 3A and the configuration of the detector for sample analysis is shown in FIG. 3B. The spectrograph detector 100a also includes a light source 14, a focusing mirror 16, a sample cell 34, a collection mirror 110, an entrance slit 102, a diffraction grating 104 and a photodiode array (PDA) 108. It should be noted that in general reference should be made to the foregoing discussion of FIGS. 1,2 for those components having common reference numerals.

Referring now only to FIG. 3B, the light 101 emanating from the light source 14 is focused onto the entrance lens 36 of the flow cell 34 by the focusing mirror 16 preferably so the full spectrum of this light impinges upon the fluid sample within the flow cell. The light 103 exiting the flow cell 34 passes to a collection mirror and then onto an entrance slit 102. The light passing through the entrance slit 102 is directed to a diffraction grating 104.

The spectrograph entrance light 103 is diffracted by the grating 104, as is known in the art, to spread the spectrum out along the face of the photodiode array (PDA) 108. In an exemplary embodiment, the diffraction grating diffracts the light 103 in the range from about 190 nm to about 800 nm. As is also known in the art, the PDA 108 includes a plurality of pixels or strips so as to simultaneously sense a plurality of bandpasses in a specified range of wavelengths or frequencies. Thus, the entire spectrum of the light 103 exiting from the sample cell 34 is sensed by the PDA 108 at the same time. As described above for the photodetector assembly 40, the signal output of each pixel or strip of the PDA 108 is processed further, such as digitizing, measuring and displaying the results as is known in the art.

The spectrograph detector 100*a* is calibrated to establish a relationship between each wavelength of light being diffracted (i.e., center wavelength of a bandpass) and each pixel or strip of the PDA 108 that represents a bandpass. Referring now to FIG. 3A, calibration of the spectrographic detector 100*a* is begun by placing (e.g. rotating) the calibration medium 12 so it is disposed in the light beam 101 from the light source 14 and is between the light source and the sample cell 34.

As indicated above, the calibration medium 12 is a rare-earth doped gel-silica base glass monolith that exhibits a known absorption spectrum which includes a plurality of spectral features. Thus, a light beam 101' having a composite spectrum, such as that shown in FIG. 7, exits the calibration medium 12. Because an optically neutral material is disposed within the flow cell 34 when calibrating a detector 100*a,* light having the composite spectrum passes onto the diffraction grating 104.

The diffraction grating 104, as described above spreads the composite spectrum out across the PDA 108 so the composite light spectrum is discretely and simultaneously sensed in each one of the plurality of bandpasses. The processed spectral data output from the PDA 108 is used by the end user, field service representative or technician to establish or define the center wavelength for each pixel or strip of the PDA 108. For example, the spectrum derived from the spectral data output is evaluated to identify the pixel location of each known spectral features in the composite spectrum and to assign a wavelength to the individual pixels based on this information.

In a specific embodiment, the diffraction grating 104 is mounted upon an adjustable mount 106. This allows the end user or technician to adjust the range of the light being diffracted.

Figure 3C:
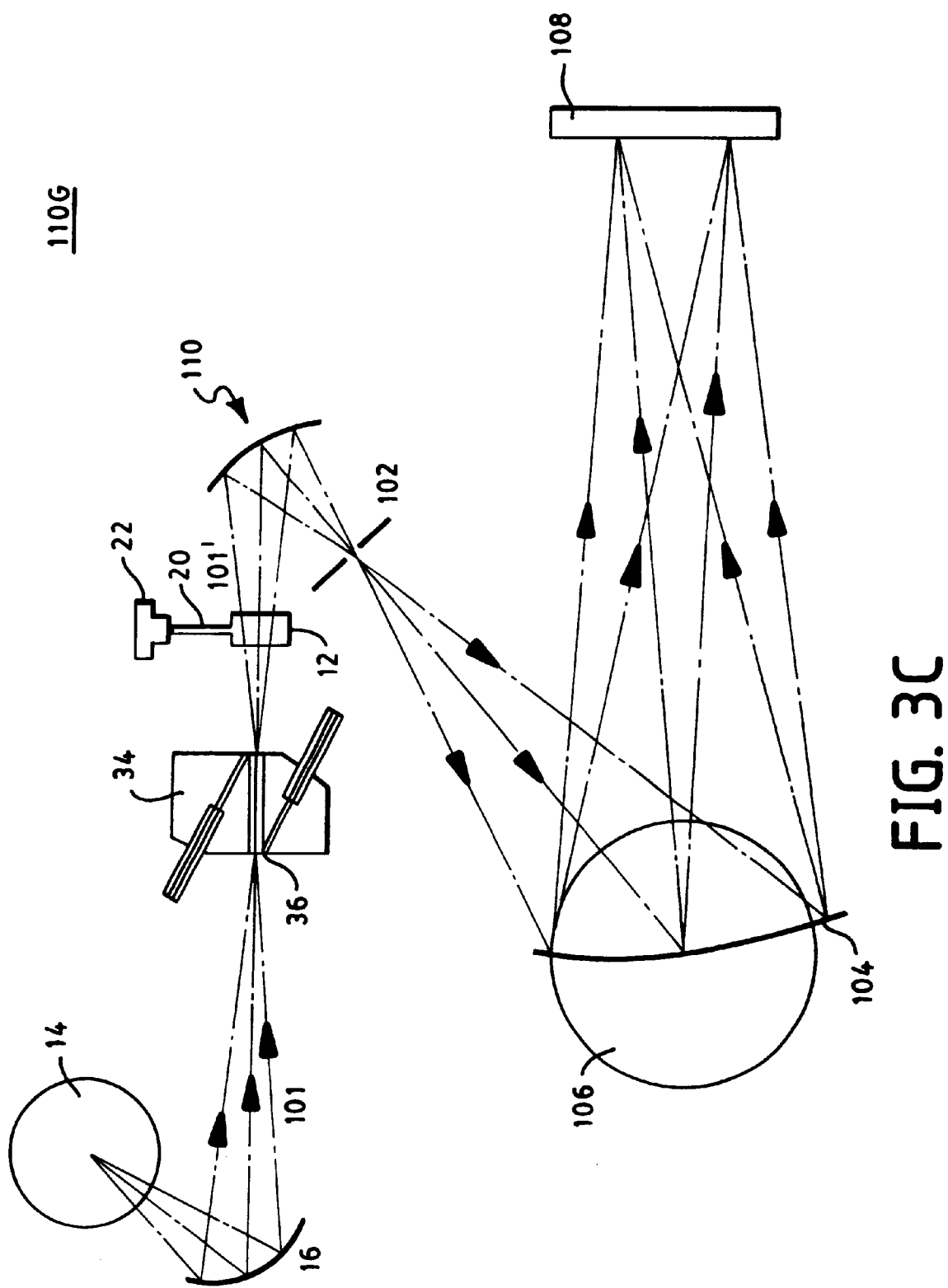
FIG. 3C is an optical schematic diagram of an alternate configuration for the spectrograph detector of FIG. 3A.
Figure 3D:
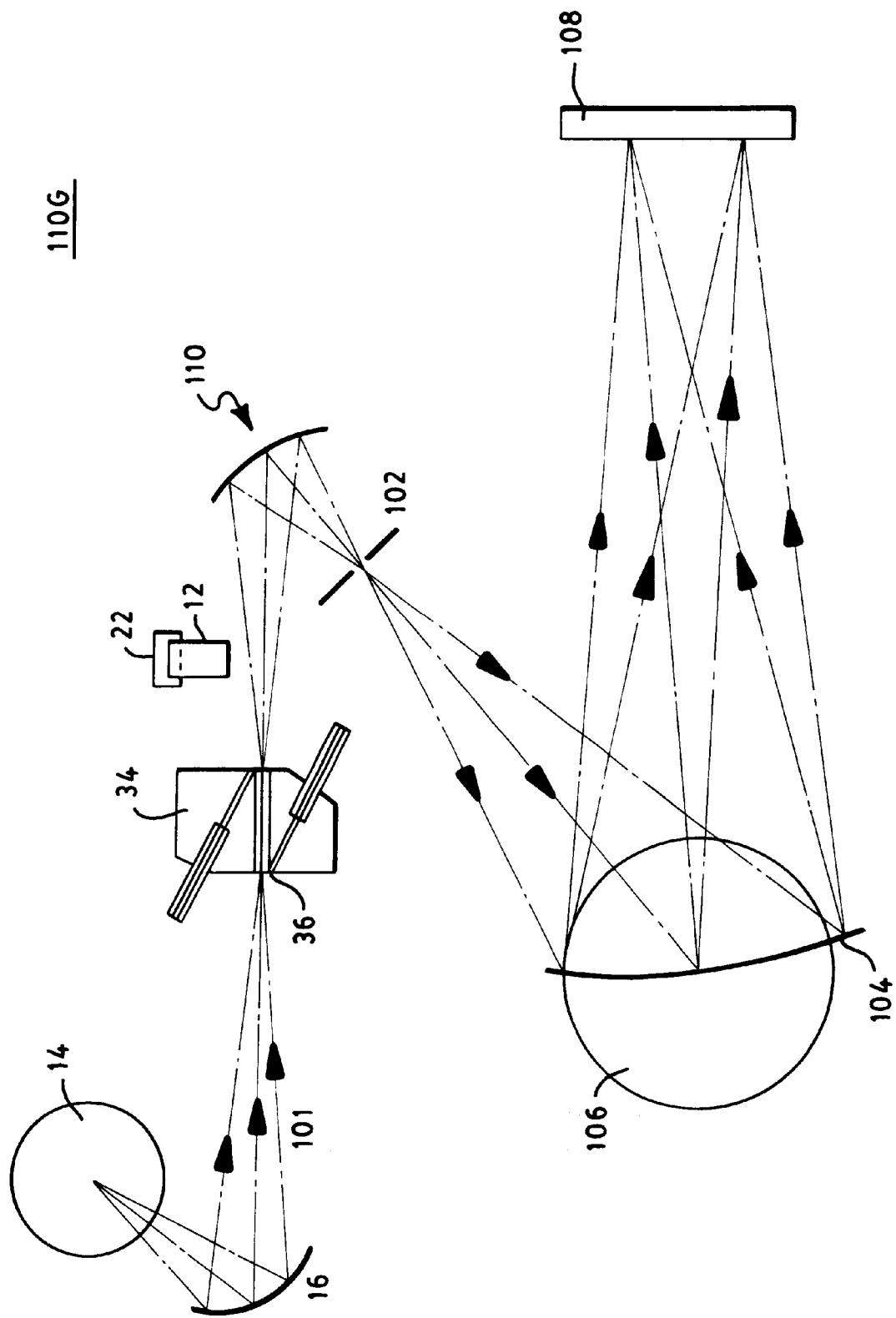
FIG. 3D is an optical schematic diagram of the spectrograph of FIG. 3C when configured for analysis.

Referring now to FIGS. 3C,D there is shown an optical schematic diagram of an alternate configuration for an exemplary calibratable spectrograph detector 10*b*. In this configuration or arrangement, the calibration medium 12 is located so that in the second position, as shown in FIG. 3C, it is disposed between the sample cell 34 and the spectrograph entrance slit 102. Also, in this configuration the spectrum of the light that impinges upon the sample cell 34 is that of the light source 14 only. In all other respects the above discussion regarding the structure, operation and calibration of the detector 100*a* of FIGS. 3A,B applies equally to the detector 100*b* illustrated in FIGS. 3C,D.

Although the foregoing calibration process has been described in terms of a manual operation by a technician, this is not a limitation. It is within the scope of the instant invention for the spectrographic detector 100*a,b* to be configured with a digitizer, a central processing unit, storage memory and an applications program(s) that automatically rotates the calibration medium into and out of the light beam, acquires and analyzes the spectral data and establishes a look up table with the relationship between wavelength and the PDA's pixel position.

The foregoing describes the use of a rare-earth doped gel-silica base glass monolith as a calibration medium for specific types of UV absorbance detectors and one specific technique for forming a sol-gel silica base glass monolith. This, however, is not a limitation. It is within the scope of the instant invention for the above described teachings of the instant invention, including the above described calibration medium, to be used to calibrate any of a number of detectors, detection systems, instruments, analysis apparatuses. In particular, such detectors, detection systems, instruments, analysis apparatuses that are particularly adapted or configured to sense spectral emissions extending into the far UV range. This includes, but is not limited to, tunable UV absorbance detectors, PDA based absorbance detectors, UV spectrophotometers and fluorescence detectors. It also is within the scope of the instant invention for the calibration medium to be made using any of a number of other specific sol-gel processes or manufacturing techniques.

While a preferred embodiment of the invention has been described using specific terms, such description is for illustrative purposes only, and it is to be understood that changes and variations may be made without departing from the spirit or scope of the following claims.

What is claimed is:

1. An optical instrument comprising:
    a spectral light source, wherein said light source emits light in the far UV range, wherein said light travels along a light path, and wherein said light has at least one wavelength;
    a means for receiving a sample within said light path;
    a sensor assembly, wherein said sensor assembly produces a signal upon receiving light, and
    a calibration medium, wherein said calibration medium assumes a position in said light path between said spectral light source and said sensor assembly, wherein said calibration medium comprises:
    a gel-silica based glass monolith, wherein said gel-silica based monolith is a type IV porous gel-silica base glass, wherein said type IV porous gel-silica base glass has a UV transmittance of about 50% at 250 nm, and
    a rare-earth material dopant, wherein said rare-earth material dopant is selected from the group consisting of atoms of a rare-earth class that have partially filled 4*f* electron shells.

2. The optical instrument of claim 1, wherein said type IV porous gel-silica base glass is replaced with type V dense gel-silica base glass.

3. The optical instrument of claim 1, wherein said dopant is selected from the group consisting of atomic numbers 58 through 69 and 70.

4. The optical instrument of claim 3, wherein said dopant has a spectral range from about 190 nm to about 700 nm.

5. The optical instrument of claim 3, wherein said dopant is erbium.

* * * * *